(12) United States Patent
Chan et al.

(10) Patent No.: US 7,894,888 B2
(45) Date of Patent: Feb. 22, 2011

(54) DEVICE AND METHOD FOR MEASURING THREE-LEAD ECG IN A WRISTWATCH

(75) Inventors: Hsiao-Lung Chan, Gueishan Township, Taoyuan County (TW); Pei-Kuang Chao, Gueishan Township, Taoyuan County (TW); Jia-Chen Jheng, Gueishan Township, Taoyuan County (TW)

(73) Assignee: Chang Gung University, Taoyuan County (TW)

( * ) Notice: Subject to any disclaimer, the term of this patent is extended or adjusted under 35 U.S.C. 154(b) by 177 days.

(21) Appl. No.: 12/236,558

(22) Filed: Sep. 24, 2008

(65) Prior Publication Data

US 2010/0076331 A1    Mar. 25, 2010

(51) Int. Cl.
*A61B 5/04* (2006.01)
(52) U.S. Cl. ..................................................... 600/509
(58) Field of Classification Search .................. 600/301, 600/508, 509, 485, 595
See application file for complete search history.

(56) References Cited

U.S. PATENT DOCUMENTS

| | | | | |
|---|---|---|---|---|
| 4,120,294 A | * | 10/1978 | Wolfe | 600/519 |
| 5,515,858 A | * | 5/1996 | Myllymaki | 600/301 |
| 5,613,495 A | * | 3/1997 | Mills et al. | 600/509 |
| 6,832,109 B2 | * | 12/2004 | Nissila | 600/509 |
| 7,171,259 B2 | * | 1/2007 | Rytky | 600/509 |
| 2008/0287751 A1 | * | 11/2008 | Stivoric et al. | 600/301 |

\* cited by examiner

*Primary Examiner*—Carl H Layno
*Assistant Examiner*—Brian T Gedeon

(57) ABSTRACT

A wristwatch worn by a user for measuring a three-lead ECG includes three electrodes placed separately on the front, either side, and back or strap thereof. The wristwatch further includes an electrode panel having the electrode on the front or either side of the watch, sensing elements, pressure, infrared or impedance detectors, and circuits. The electrode panel is capable of sensing the contact or press of fingers to trigger the ECG measuring. While the electrode in the back-side of the watch contacts the hand wearing the watch, the electrode and electrode panel on the front or either side of the watch are pressed by fingers from the other hand, and the electrode in the strap contacts the abdomen or left leg simultaneously. Thus, a three-lead ECG can be measured. ECG data can be transmitted to a personal or hospital computer by wireless networks or flash memory.

19 Claims, 14 Drawing Sheets

DEVICE AND METHOD FOR MEASURING THREE-LEAD ECG IN A WRISTWATCH

BACKGROUND OF THE INVENTION

1. Field of Invention

This invention relates to a wristwatch with the function of measuring and processing a three-lead electrocardiogram (ECG) and more particularly, to a wrist-watch that is capable of measuring a three-lead ECG and providing event-related reminders for alerting users to measure an ECG in a critical moment determined by a sensing system or by the user. In addition, this invention is related to a method for measuring the three-lead ECG by the wristwatch.

2. Description of Related Art

Regularly tracking on changes in cardiac function is usually suggested for the elderly to maintain fitness. In a hospital, a three-lead ECG measurement has been widely used to monitor cardiac function. While accepting a cardiac assessment in the hospital, it can often cost time, can increase the risk to get an infection and may not be convenient for the elderly. To be capable of measuring an ECG conveniently, portable ECG recording devices have been developed.

Although portable ECG measuring devices have been introduced to record an ECG outside a hospital, the need to wear electrodes on the chest and carry cables connecting to the device makes it difficult to use on an ambulatory and daily base. Some wristwatches have been made for measuring heart rates or heart pulses but have not been equipped with a three-lead ECG measurement and arrhythmia analysis which provides more detail information about the cardiac system.

A standard three-lead ECG indicates a measurement of cardiac potentials leaving from the heart in 3 directions, toward the right-arm (RA), toward the left-arm (LA), and toward the left leg (LL). The lead I of the ECG is the cardiac potential difference between LA and RA (LA−RA), the lead II of the ECG is the cardiac potential difference between LL and RA (LL−RA), and the lead III of the ECG is the cardiac potential difference between LL and LA (LL−LA). Also, 3 augmented leads (lead AVR, AVL and AVF) can be calculated based on the standard three-lead ECG. Lead AVR is RA−(LA+LL)/2=−(I+II)/2, lead AVL is LA−(RA+LL)/2=(I−III)/2, and lead AVF is LL−(RA+LA)/2=(II+III)/2.

To meet the need of convenience and medical expertise, it is desirable to have a portable device, e.g. a wristwatch, which can measure and process a three-lead ECG without extra cable connections. Further, the three-lead ECG data acquired by a portable device, which can be recorded and transmitted to a personal and hospital computer, will be highly convenient and needed.

SUMMARY OF THE INVENTION

The object of this invention is to provide a portable device, a wristwatch, with the function of measuring, recording, and analyzing a three-lead ECG. Three electrodes are placed on the front-side/lateral-side, the back-side, and the strap of the watch separately. When the watch is worn, the electrode in the back-side of the watch contacts the first hand which wears the watch. Then, a finger from the second hand contacting the electrode on the front-side of the watch can form an electrical loop to measure the lead I of ECG (ECG potential difference between right and left arms). To measure the other 2 ECG leads, the wearer needs to bring the electrode on the strap to touch his/her own abdominal area or left leg, while the fingers from the second hand still press on the electrode on the front-side of the watch to form a triangle electrical loop. The potential difference between each pair of electrodes represents a lead. The lead I of ECG is the potential difference between the left arm and right arm, the lead II of ECG is the potential difference between the left leg (or abdomen) and right arm and the lead III of ECG is the potential difference between the left arm and left leg (or abdomen). Therefore, a standard three-lead ECG can be obtained based on the 3 electrodes. In addition, the trigger to start an ECG measurement is an electrode panel that comprises sensing elements on the front-side/lateral-side of the watch. The sensing elements can be detectors of pressure, impedance or infrared to recognize the contact or press of a finger. The watch has the function of providing reminders, which can be sound, light, vibration or all of them, to notify the user to measure an ECG. The events which can induce reminders comprise alarm setups, activity levels, temperature changes, etc. and temperature changes etc.

DETAILED DESCRIPTION OF THE INVENTION

Figures 1A, 1B:
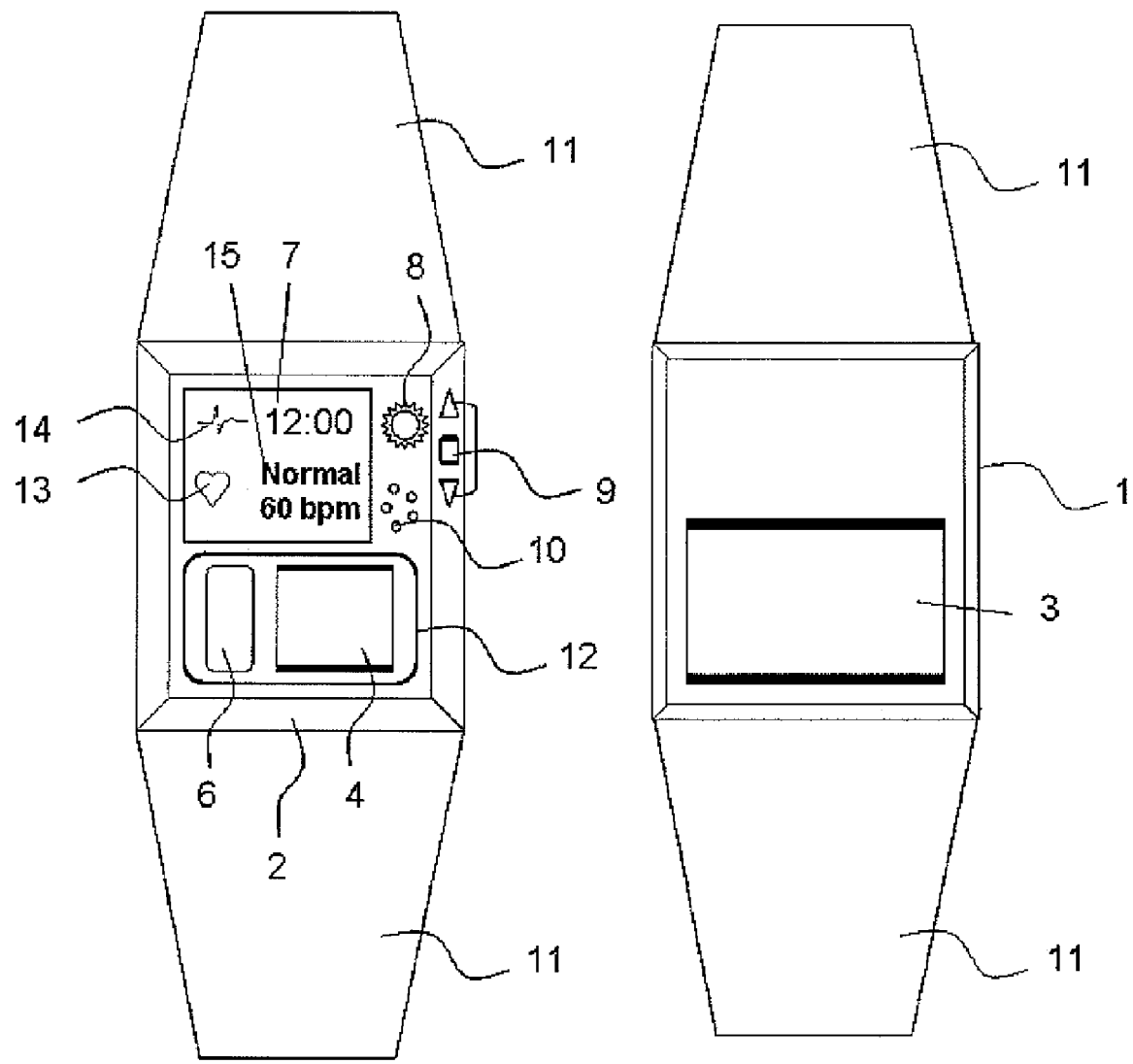
FIGS. 1A and 1B show front and back views of one embodiment of the invention.

Referring to FIGS. 1A and 1B, there are shown views of a preferred embodiment of the invention including back-side 1 and a front-side 2 of the wristwatch. In the back-side 1 of the watch, an electrode 3 is inserted for touching the hand which wears the watch. In the front-side 2 of the watch, there is another electrode 4 for fingers from the other hand to press on, while the watch is worn on one hand. An electrode panel 12, comprising the electrode 4 on the front-side 2 of the watch and sensing elements 6, is placed on the front-side 2 of the watch. The sensing elements 6 can detect pressure, impedance or infrared for recognizing the contact or press made by fingers to initiate an ECG measurement. A display 7, such as a liquid crystal display (LCD), is on the front-side 2 of the watch. The display 7 can demonstrate in text 15, which includes time, heart rate, condition (normal or arrhythmia), and graph/animation, for an event reminding 13 and ECG waveforms 14. To modify watch function and displaying contents, at least 1 control button 9 is set on the watch. To exhibit event-related reminders, output devices for light 8 (for example, light emitting diode (LED), LCD, organic light emitting diode (OLED)) and/or sound 10 (for example, a miniature buzzer or speaker) may be positioned in the watch with an opening on the watch surface. The watch can also have a miniature motor inside to provide the function of vibration as a reminder.

Figure 2:
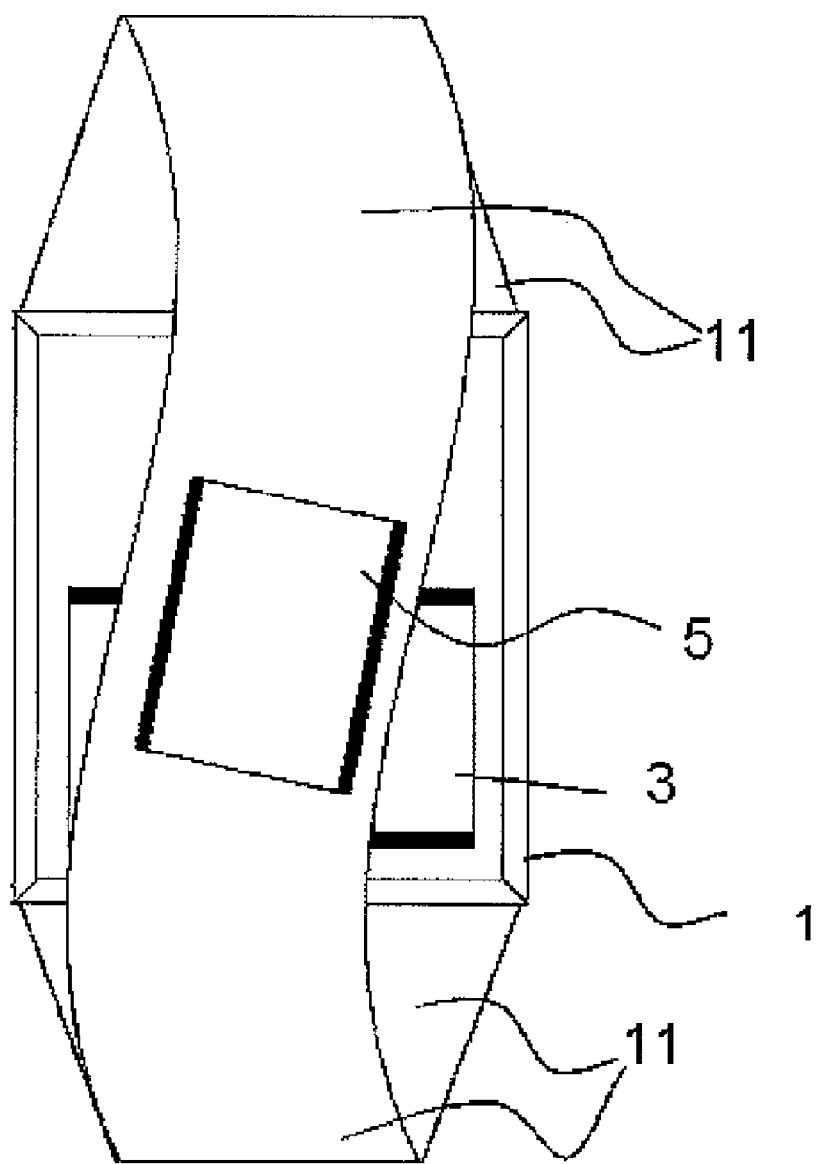
FIG. 2 shows a back view of one embodiment to present a location of the electrode on the strap.

Referring to FIG. 2, an electrode 5 is placed on the outer side of the strap 11 of the watch for making connection with the left leg or abdomen to form electrical loops for a three-lead ECG measurement.

Figure 3A:
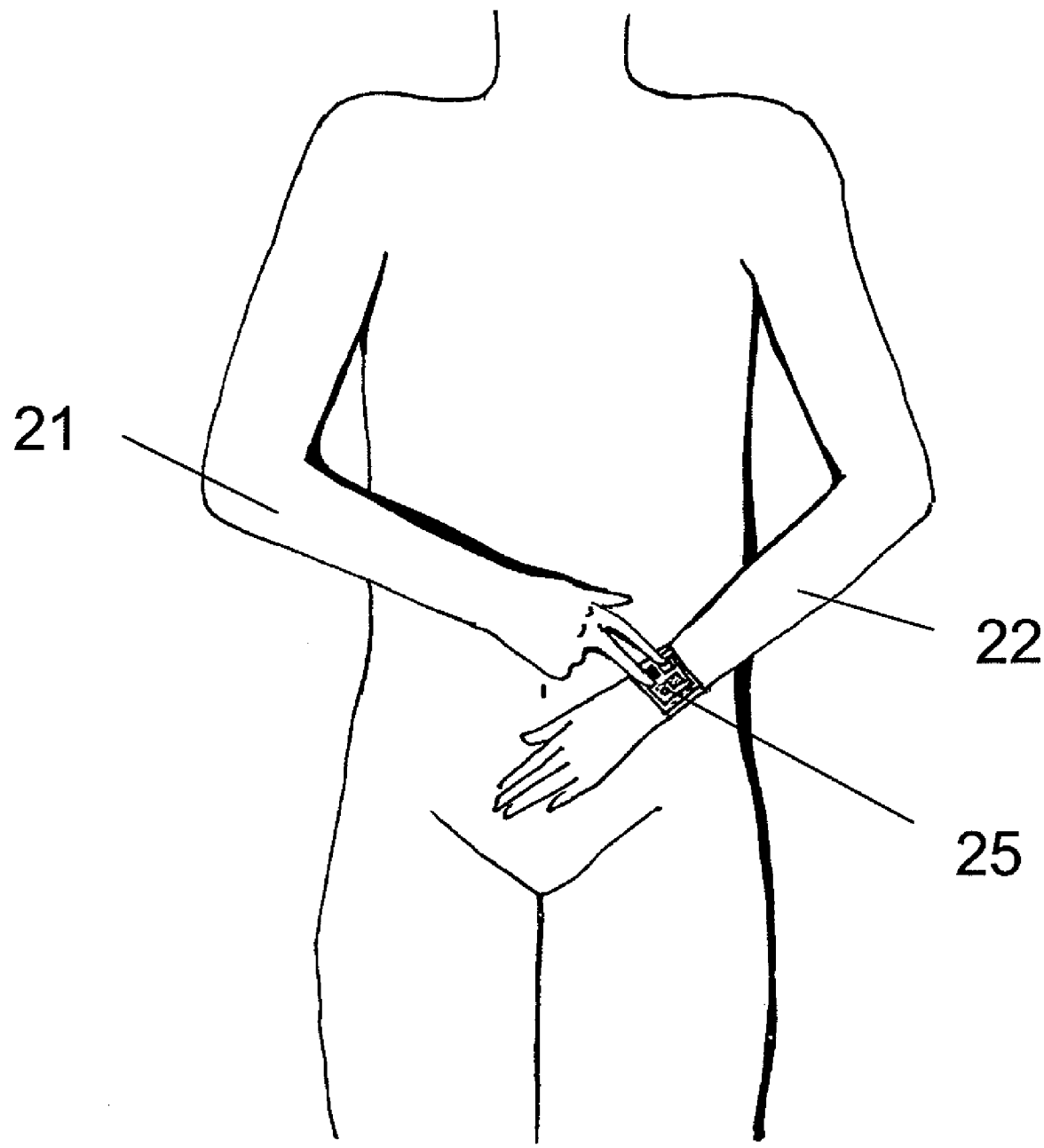
FIGS. 3A, 3B, 3C, and 3D show an example of the use of the invention and demonstrate how to place the wristwatch to make electrodes be contacted by both hands and abdomen.
Figure 3B:
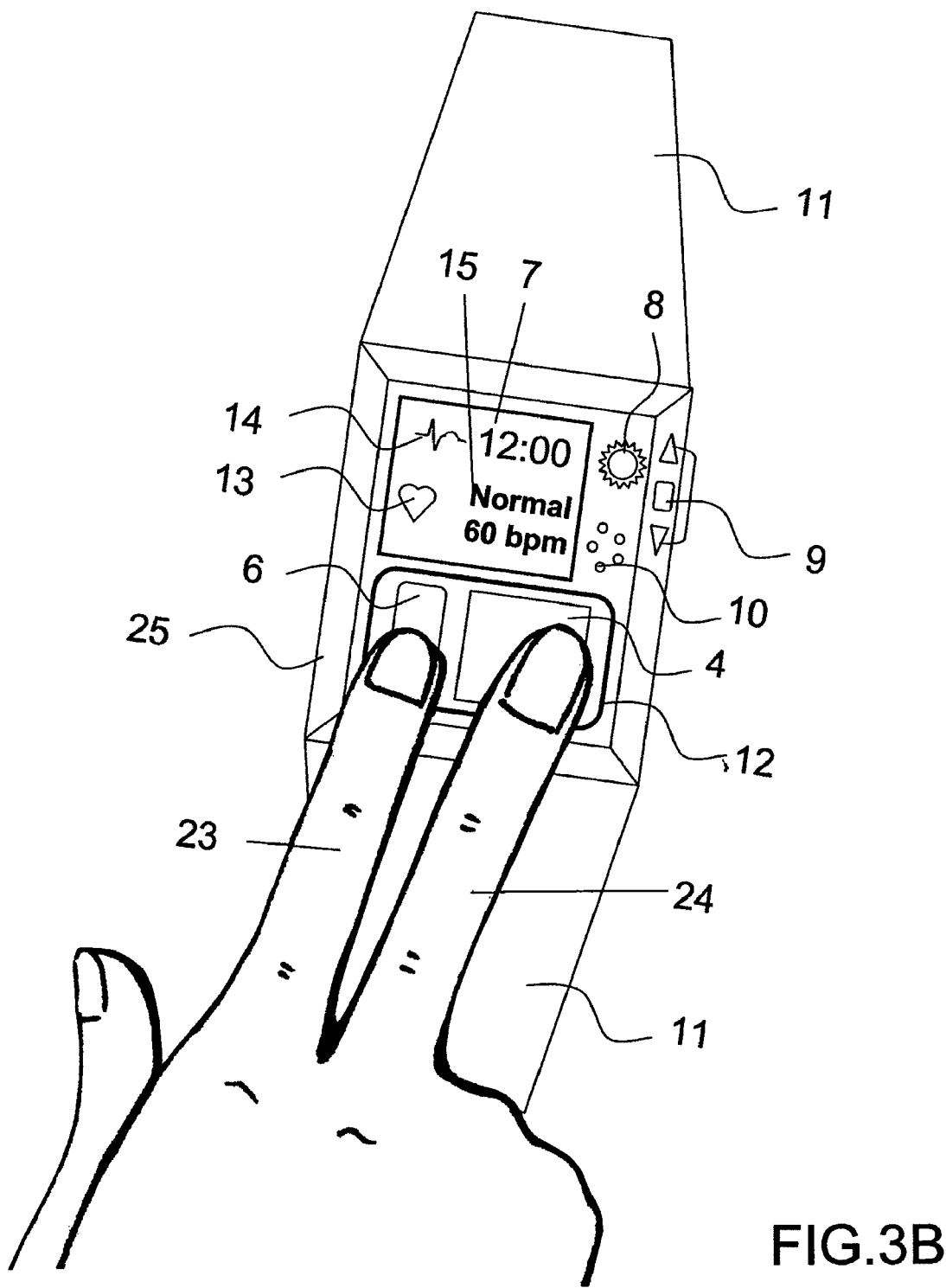
Figure 3C:
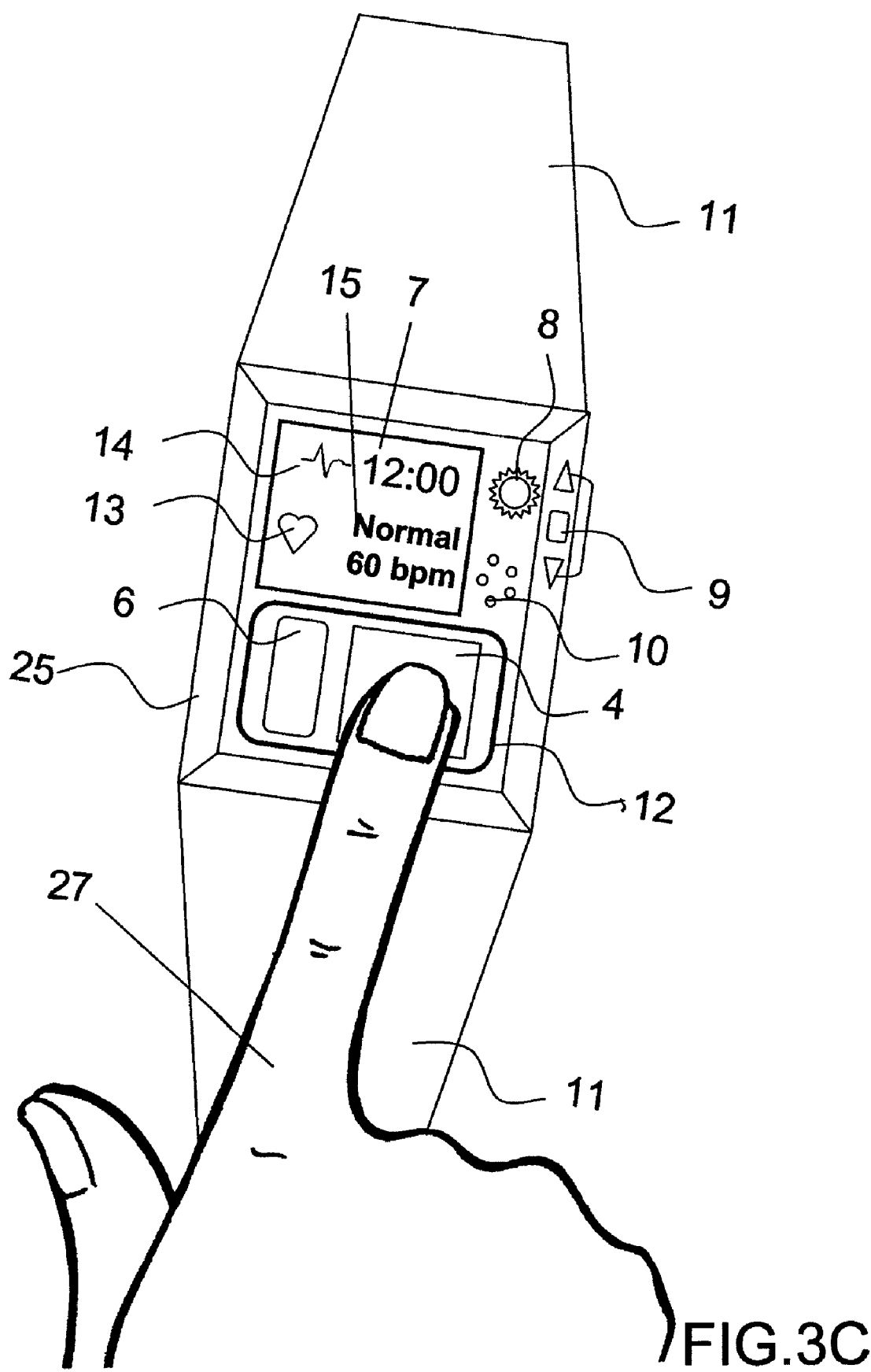
Figure 3D:
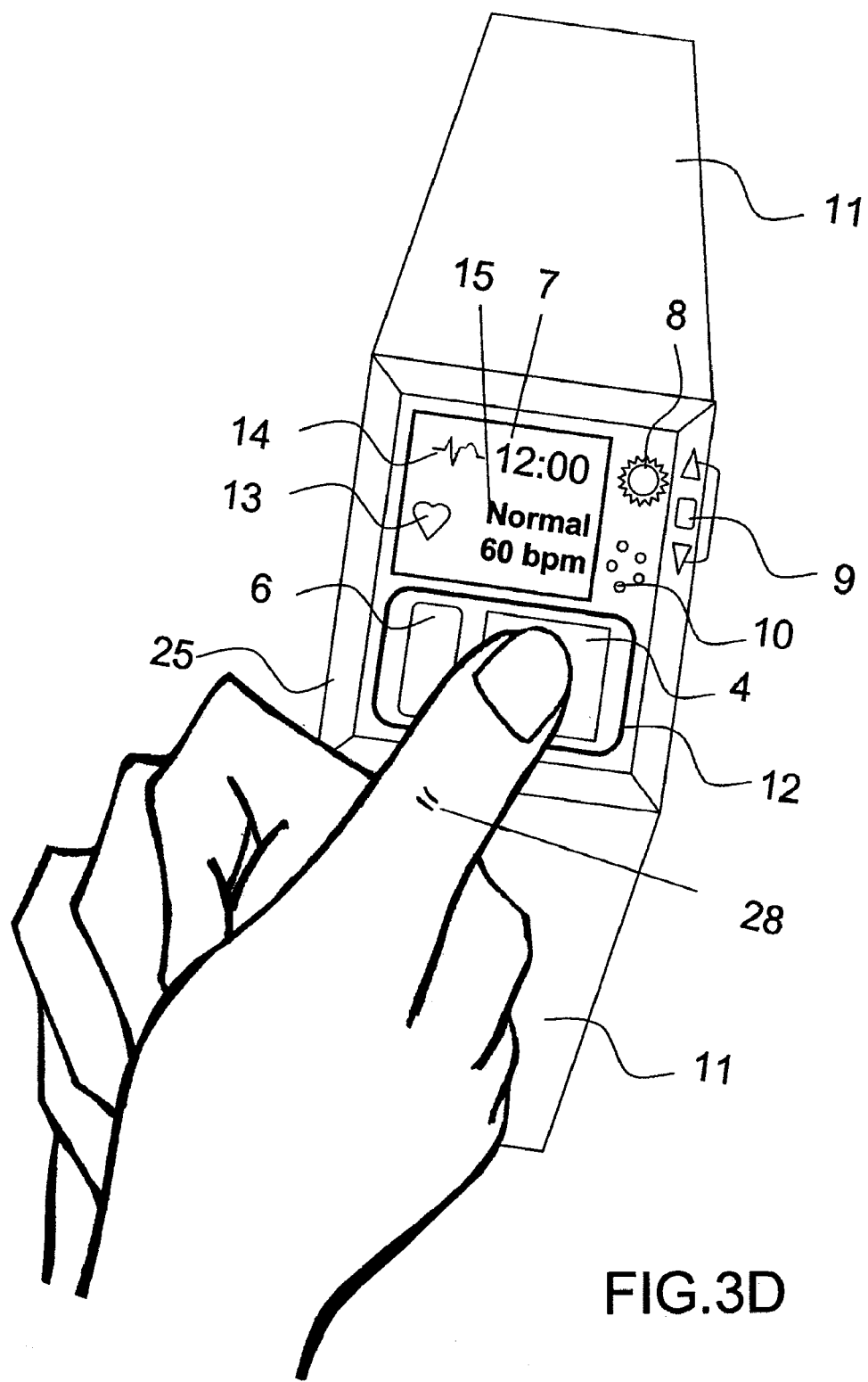

Referring to FIGS. 3A to 3D, one of the methods according to the invention for measuring three-lead ECG is illustrated. The watch 25 is worn tightly on one hand 22 (FIG. 3A). In FIG. 3B, one finger 23 from the other hand 21 presses on the sensing elements 6, and another finger 24 from the other hand 21 presses on the electrode 4 on the front 2 of the watch simultaneously. At the same time, the electrode 5 (as shown in FIG. 2) on the strap 11 of the watch 25 contacts the skin in the wearer's abdominal area to form a triangle electrical loop. In addition, the placement of fingers can be altered to be one finger (any one finger 27 from the other hand in FIG. 3C, or the thumb 28 from the other hand in FIG. 3D) touching both the sensing elements 6 and electrode 4 on the electrode panel 12 to trigger and make a measurement. After measuring an ECG, the data obtained can be stored in a flash memory plugged or inserted in the watch and/or transmitted via a wireless module 56 to a personal computer or hospital computer 62.

Figure 4A:
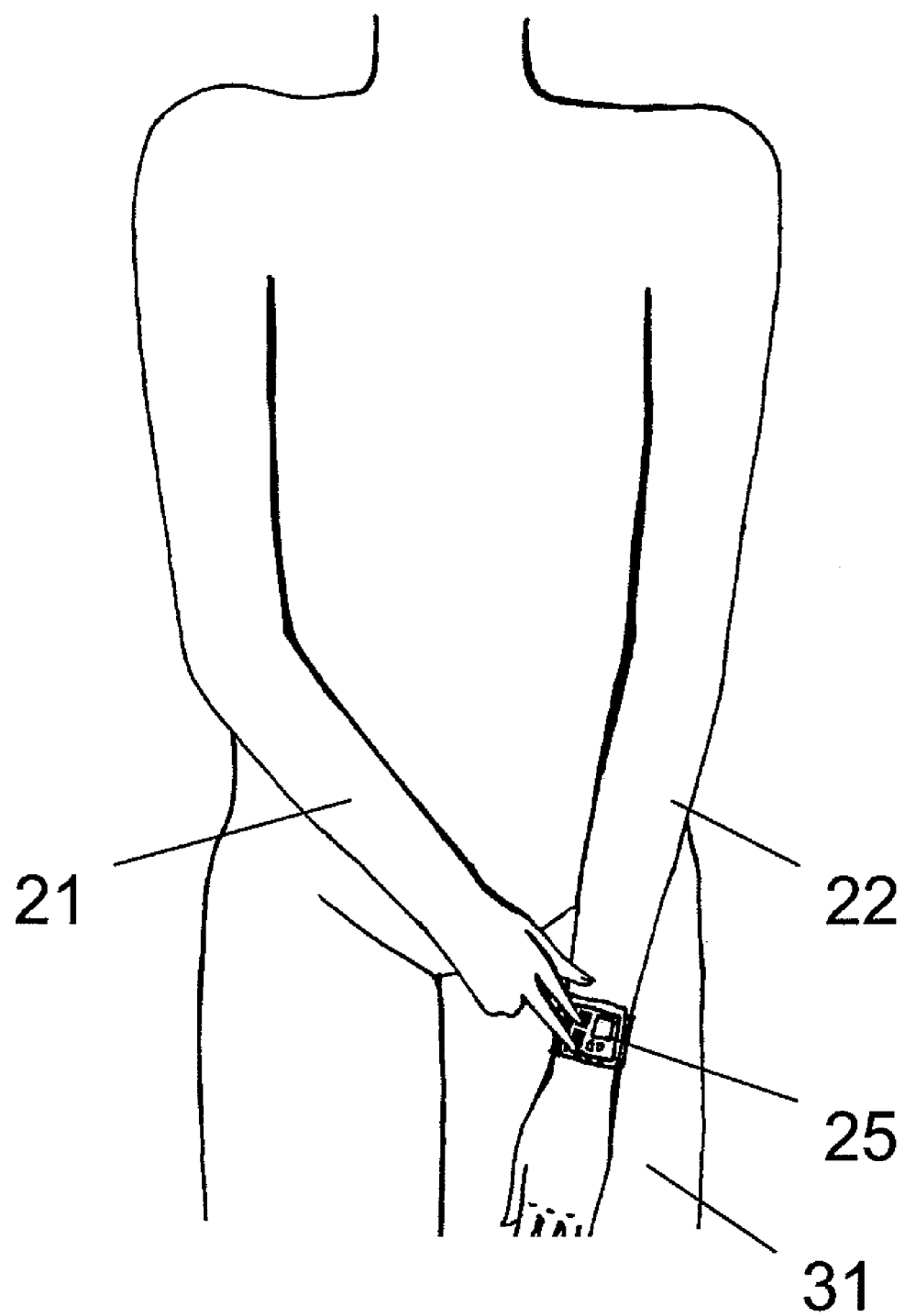
FIGS. 4A, 4B, 4C, and 4D show another example of the use of the invention and demonstrate how to place the wristwatch to make electrodes be contacted by both hands and left leg.
Figure 4B:
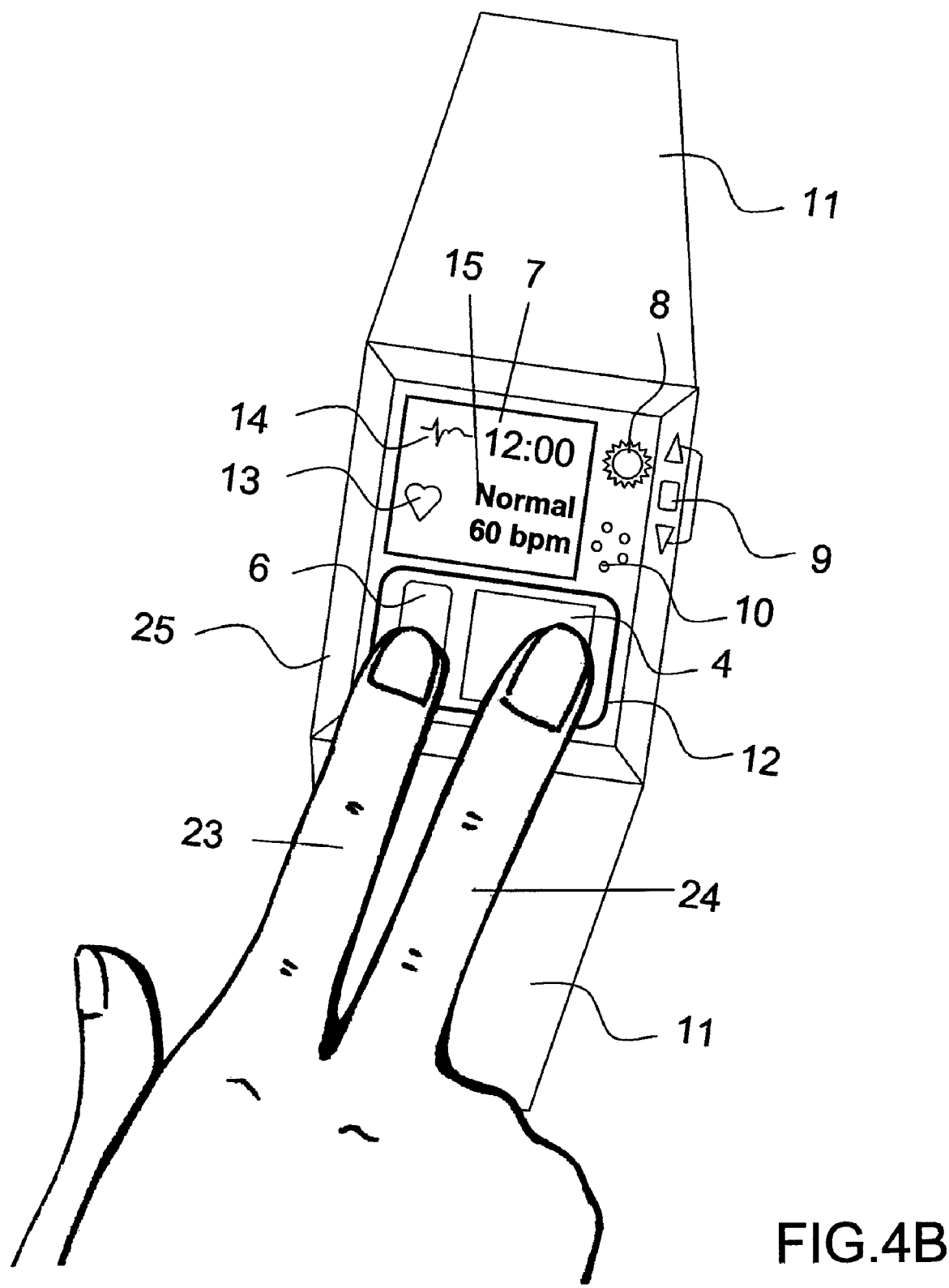
Figure 4C:
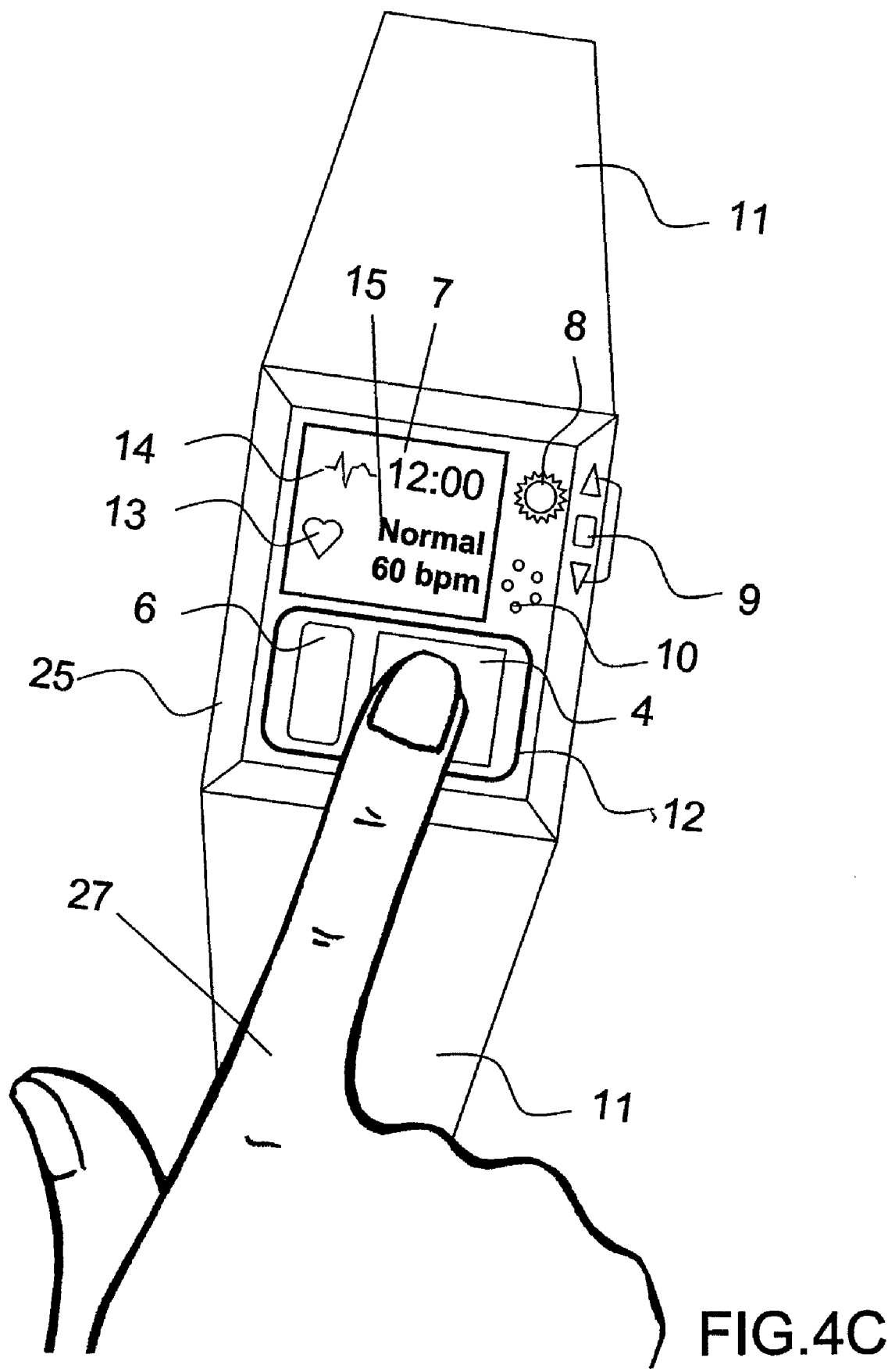
Figure 4D:
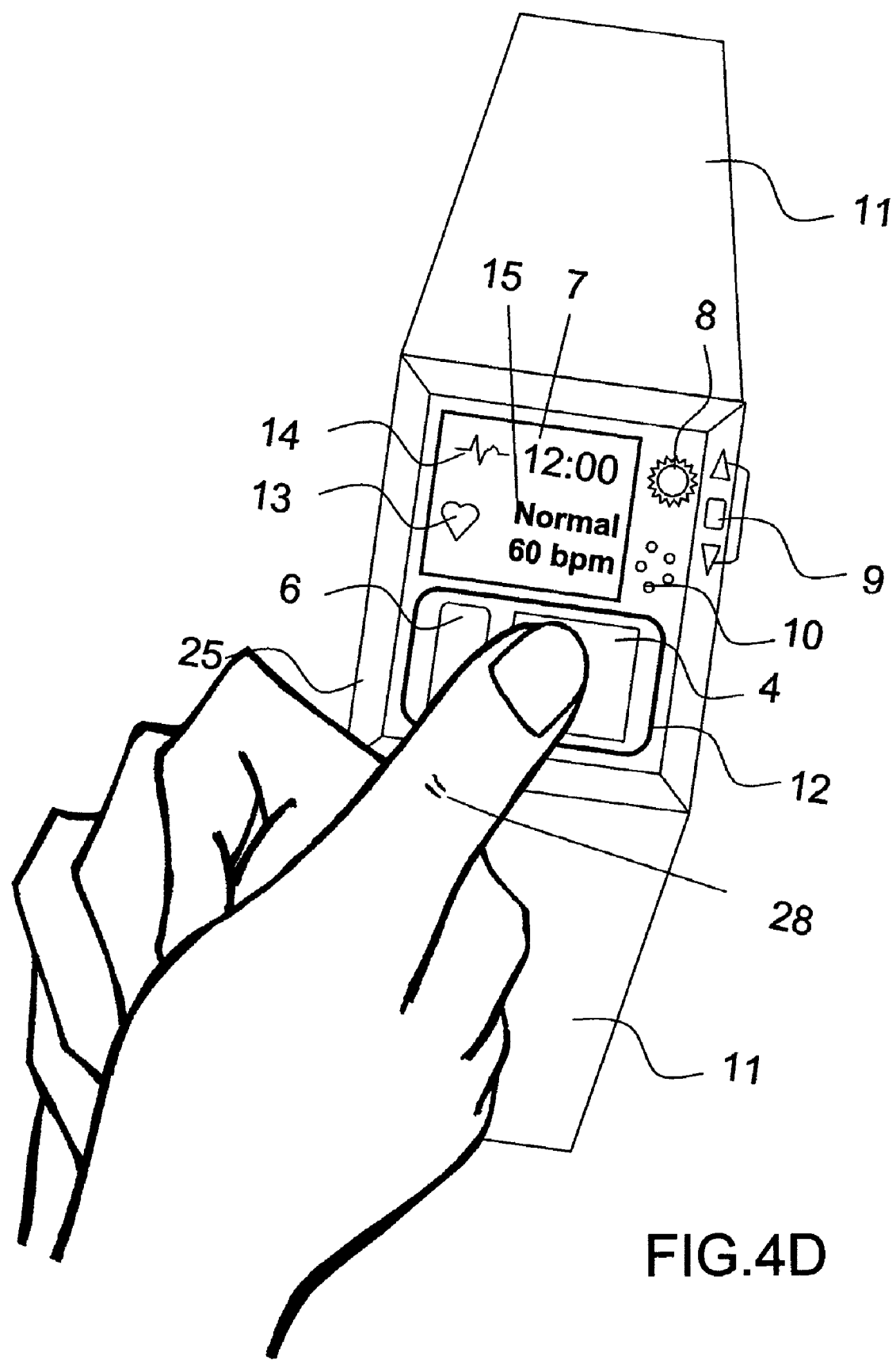

Referring to FIGS. 4A to 4D, another method according to the invention for measuring a three-lead ECG is illustrated. The watch is worn tightly on one hand 22 (FIG. 4A). In FIG. 4B, one finger 23 from the other hand 21 presses on the sensing elements 6, and another finger 24 from the other hand 21 presses on the electrode 4 on the front 2 of the watch simultaneously. At the same time, the electrode 5 (as shown in FIG. 1) on the wrist-band 11 of the watch contacts the skin on the wearer's left thigh area 31 to form a triangle electrical loop. In addition, the placement of fingers can be altered to be one finger (any one finger 27 from the other hand in FIG. 4C, or the thumb 28 from the other hand in FIG. 4D) touching both the sensing elements 6 and electrode 4 on the electrode panel 12 to trigger and make a measurement. After measuring an ECG, the data obtained can be stored in a flash memory plugged or inserted in the watch and/or transmitted via a wireless module 56 to a personal computer or hospital computer 62.

Figure 5A:
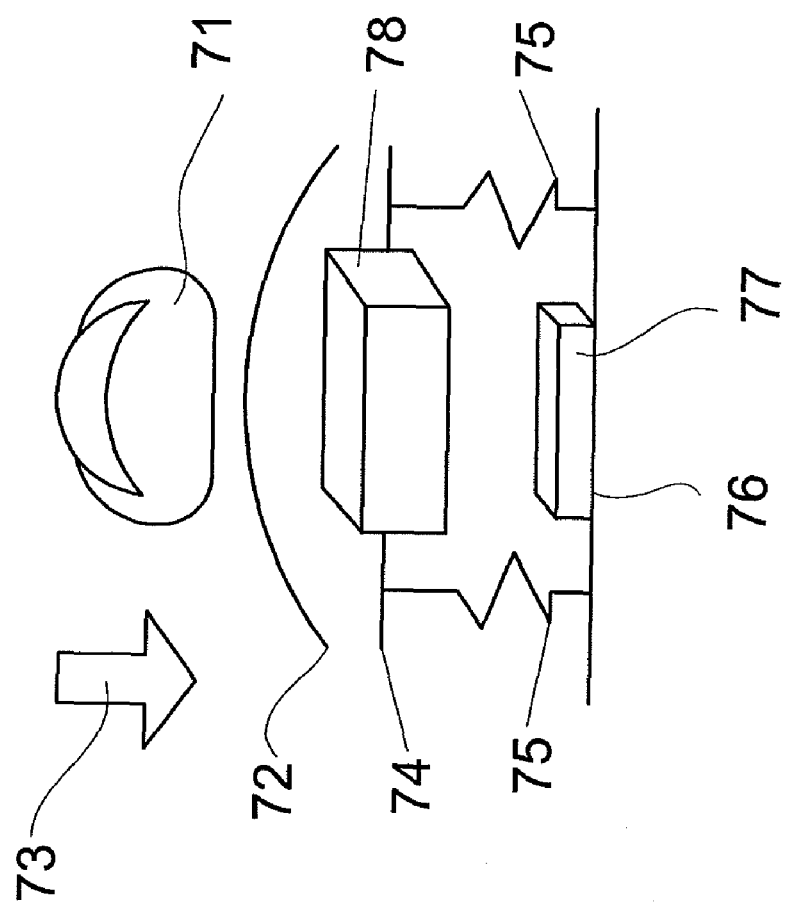
FIGS. 5A, 5B, and 5C show examples of the structures of the sensing elements.
Figure 5C:
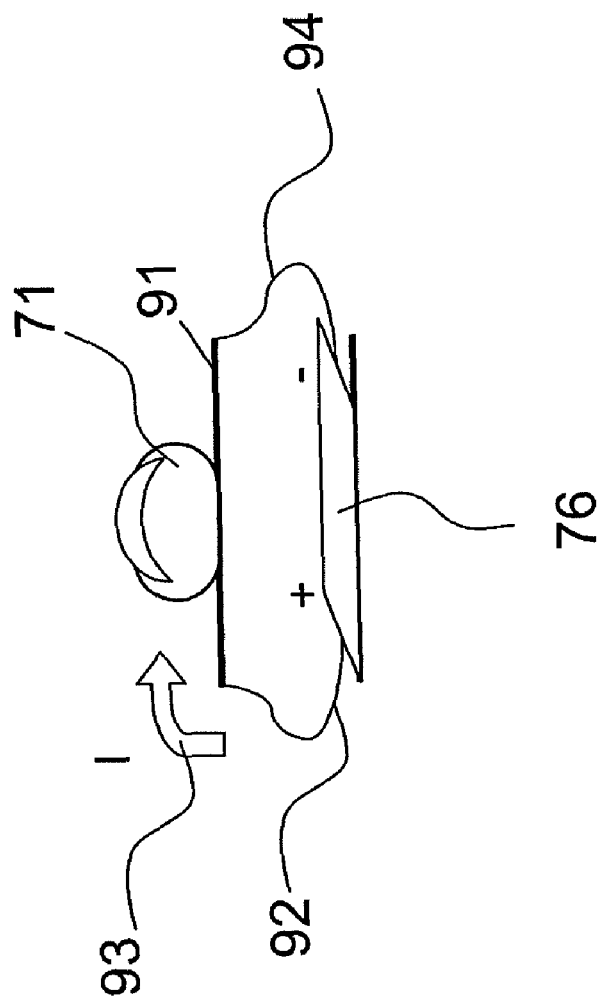
Figure 5B:
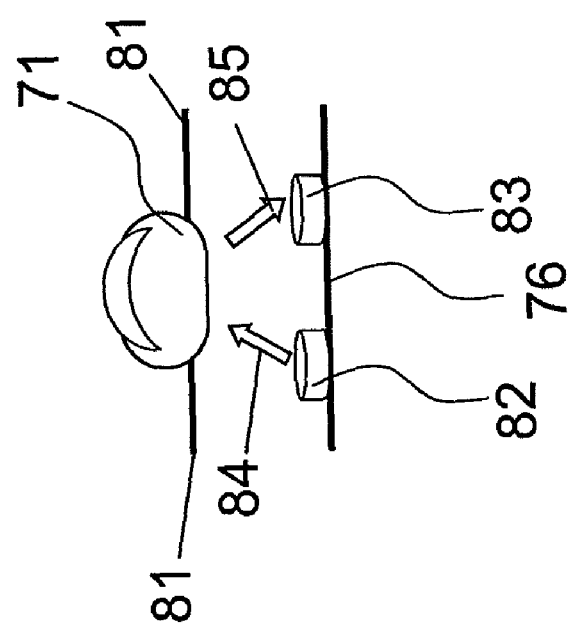

Referring to FIGS. 5A to 5C, 3 examples of sensing elements are demonstrated. Firstly, FIG. 5A shows a switch sensor 77 on a circuit board 76 embedded in the watch. When one finger 71 presses in a direction 73 on a soft surface 72 of the sensing elements 6, a solid pellet 78 inserted in a floating broad 74 under the soft surface 72 is pushed down to turn on the switch 77 to start an ECG measurement. The floating broad is supported by springs 75 which stand on the circuit board 76. Secondly, FIG. 5B shows a light source 82 and a photo detector 83 on the circuit board 76 embedded in the watch. When a finger 71 is placed on a small hole which is on the surface 81 of the sensing elements 6, the light (e.g. infrared) released by the light source 82 reaches in the direction 84 the finger and reflects in the direction 85 back to the photo detector 83. After receiving light, the photo detector 83 generates a potential to initiate an ECG measurement. Thirdly, FIG. 5C shows an impedance detecting circuit is set on the circuit board 76 embedded in the watch. When one finger 71 touches a conductive surface 91 on the sensing elements 6, a low-energy current 93 released by a wire 92 goes through fingertip 71 and back to the circuit board via another wire 94. The voltage difference between the output and input currents to the circuit board 76 is used to be a trigger to start an ECG measurement.

Figure 6:
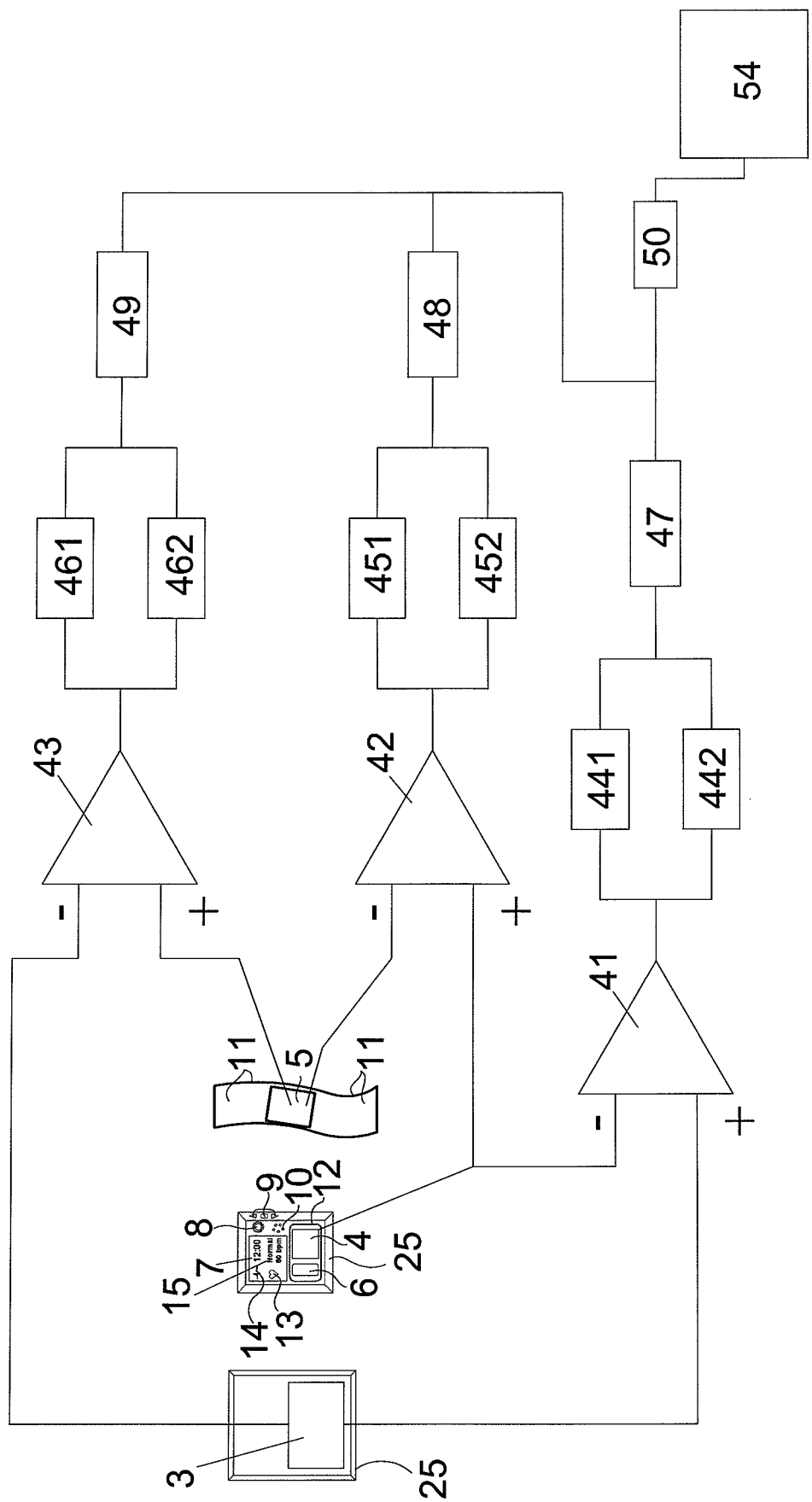
FIG. 6 shows the schematic diagram of three-lead ECG loops with right and left hand modes.

Referring to FIG. 6, the method to obtain three-lead ECG is shown. The method to compute a standard three-lead ECG is described as follows: the lead I of ECG is the cardiac potential difference between LA and RA (LA−RA), the lead II of ECG is the cardiac potential difference between LL and RA (LL−RA) and the lead III of ECG is the cardiac potential difference between LL and LA (LL−LA). In this invention, the potential difference between each pair of electrodes is obtained by differential amplifiers 41, 42, 43. The identification of ECG leads depends on which hand is wearing the watch. When the watch is worn on the left hand, the potential difference between electrodes 3, 4 on the front-side and back-side of 5 on the front-side and the band of the watch is identified as lead 451, and the potential difference between electrodes 3, 5 on the back-side and band of the watch is identified as lead III 461.

When the watch is worn on the right hand, the potential difference between electrodes 3, 4 on the front-side and back-side of the watch is identified as negative lead I 442, the potential difference between electrodes 4, 5 on the front-side and the band of the watch is identified as negative lead III 452, and the potential difference between electrodes 3, 5 on the back-side and band of the watch is identified as negative lead II 462. The reference potential of the ECG circuits is set as the combination of the signals from the 3 electrodes. All ECG data goes through filters 47, 48, 49 to sharpen signals and then an analog-to-digital converter 50 to change analog signals to be digital data for a microprocessor 54 disposed in the watch. For an augmented three-lead ECG, the calculation method is according to the standard three-lead ECG as follows: Lead AVR is $RA-(LA+LL)/2=-(I+II)/2$, lead AVL is $LA-(RA+LL)/2=(I-III)/2$, and lead AVF is $LL-(RA+LA)/2=(II+III)/2$. All circuits for ECG measuring are embedded and hidden inside the watch or the strap 11.

Figure 7:
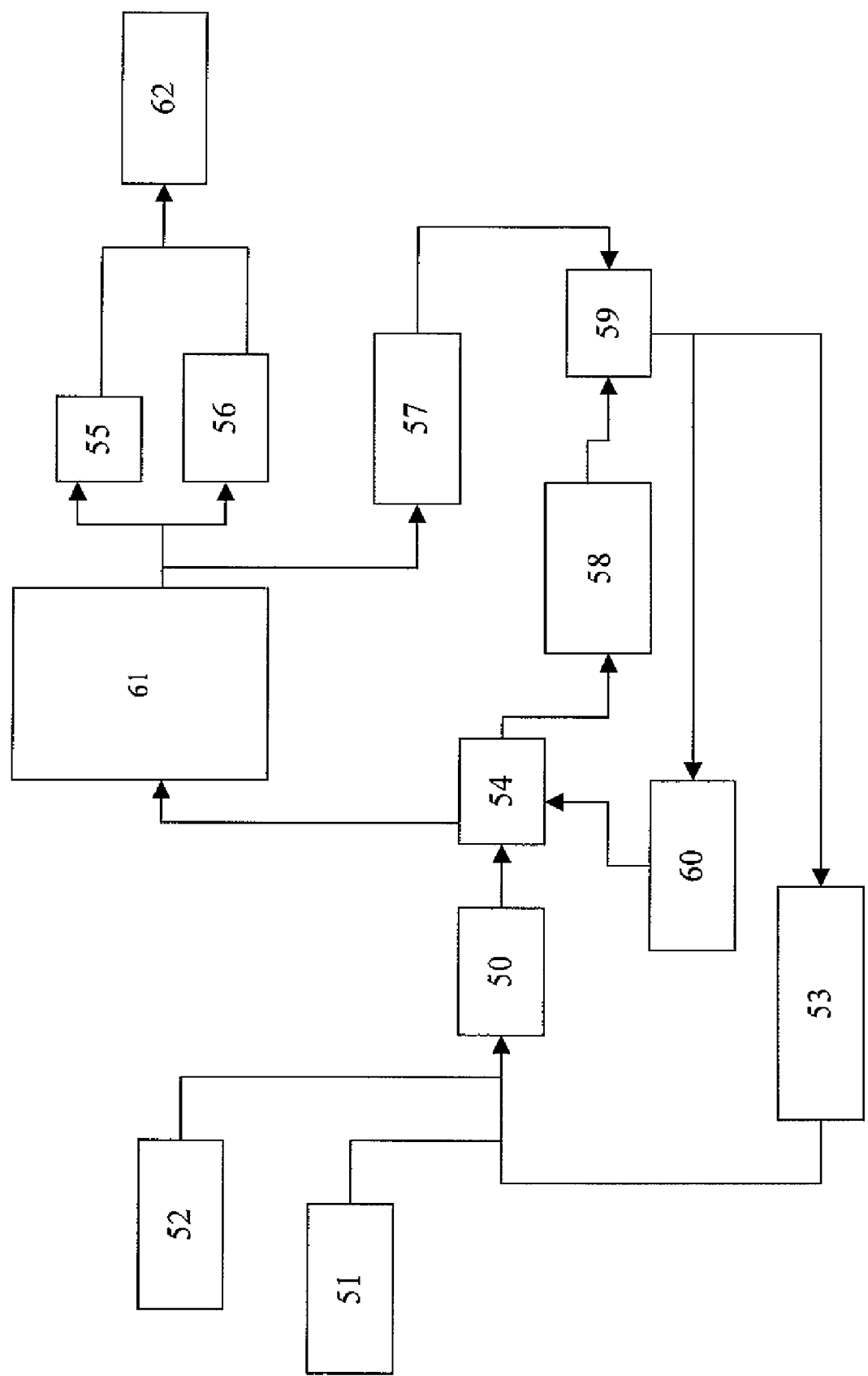
FIG. 7 shows a general block diagram illustrating one embodiment of the invention and the flow for signal collecting, processing and transferring.

Referring to FIG. 7, a general block diagram of the embodiment of the invention and the flow of signal collecting, processing and transferring is illustrated. The invention has a microprocessor 54 in the center. The inputs for inducing spontaneous reminders for users to measure an ECG can be provided by a sensing element 51 such as for activity levels and temperature changes. Activity levels are measured by the sensing element 51 in the form of an accelerometer, and temperature changes are measured by the sensing element 51 in the form of a thermometer. The signals collected by the sensing element 51 pass an A/D converter 50 before entering the microprocessor 54. When the activity level of users is intensive for a critical period of time or when the temperature changes dramatically, the microprocessor 54 will order the reminding function to be active in a form of light, sound or vibration 58 or all of them. Also, users 59 of the invention can use the control button 60 or wireless settings to set a time alarm for reminding him/her-self to measure an ECG. After receiving the reminding signals, users 59 may start an ECG measurement by pressing on the electrode panel 53 and positioning the watch as in FIG. 2 and FIG. 3 or turn off reminders by operating the control buttons 60. After measuring, ECG circuits 52 sent acquired data through the A/D converter 50 to the microprocessor 54 process and transfer data to the flash memory 55, wireless module 56, and/or display 57. The display 57 can show users 59 time, heart rate, waveforms and any other information 61, such as activity level and temperature, if needed. The data recorded in the flash memory 55 or transmitted by the wireless module 56 can eventually reach personal or hospital computers 62 for cardiac experts to make specific analyses.

A unique design and concept of a wristwatch which can measure a three-lead ECG is shown and described here. Many changes and modifications can be carried out without departing the scope of the specific embodiment described herein. The description herein is intended to be illustrated only and is not intended to be limitative. The invention is intended to be limited only by the scope of the appended claims.

What is claimed is:

1. A wristwatch for measuring a three-lead ECG, comprising:
   a case including a front side and a back side opposite to the front side;
   a strap attached to both ends of the case and including an inside surface and an outside surface, with the inside surface being intermediate the back side and the outside surface;
   a circuit board disposed in the case;
   a first electrode positioned on the outside surface of the strap;
   a second electrode positioned on the front side of the case;
   a third electrode positioned on the back side of the case, with the first, second and third electrodes being electrically separate for detecting voltage differences generated by cardiac systems, with the circuit board detecting voltage differences generated by the first and second electrodes, by the first and third electrodes, and by the second and third electrodes to obtain a set of ECG data comprising ECG lead I, ECG lead II, and ECG lead III;
   a display disposed on the case;
   a control panel comprising one of the electrodes and a plurality of sensing elements; and
   at least one control button for inputting information, changing function, and modifying user's mode of the wristwatch.

2. The wristwatch of claim 1, wherein the electrode and the sensing elements of the control panel are adapted to be touched separately.

3. The wristwatch of claim 1, wherein the control panel further includes an integrated unit covering both the electrode and the sensing elements of the control panel to allow the electrode and the sensing elements of the control panel to be activated simultaneously by one touch; wherein the integrated unit is an interface activating both the electrode and the sensing elements of the control panel by one touch.

4. The wristwatch of claim 1, further comprising an alerting device disposed in the case alerting a user to practice the ECG measurement.

5. The wristwatch of claim 4, wherein the alerting device emits light, makes sound, or vibrates.

6. The wristwatch of claim 4, wherein the alerting device is an LED or OLED emitting light.

7. The wristwatch of claim 4, wherein the alerting device is an OLED or LCD flashing light.

8. The wristwatch of claim 4, wherein the alerting device is a buzzer or speaker.

9. The wristwatch of claim 4, wherein the alerting device is a miniature vibrating motor for vibrating.

10. The wristwatch of claim 4, further comprising a sensing element measuring temperature changes as a reference value to activate the alerting device.

11. The wristwatch of claim 4, further comprising a sensing element measuring a user's activity levels as a reference value to activate the alerting device.

12. The wristwatch of claim 1, further comprising a transmission device for data transmission after the set of ECG data is obtained; with the transmission device comprising at least one of a flash memory and a wireless network for transmitting data to a remote personal or hospital computer.

13. The wristwatch of claim 1, further comprising a wireless module receiving wireless control signals from a remote computer for modifying settings of the wristwatch.

14. The wristwatch of claim 1, wherein the plurality of sensing elements are activated by infrared, pressure, or impedance.

15. The wristwatch of claim 1, wherein the circuit board processes said set of ECG data based on a wearing hand mode which includes a left-hand mode and a right-hand mode.

16. The wristwatch of claim 15, wherein when the circuit board processes said set of ECG data in said left-hand mode,
   the ECG lead I is taken as a potential difference between the second and third electrodes disposed on the back side and the front side of the case;
   the ECG lead II is taken as a potential difference between the first and second electrodes disposed on the strap and the front side of the case; and
   the ECG lead III is taken as a potential difference between the first and third electrodes disposed on the back side of the case and the strap.

17. The wristwatch of claim 15, wherein when the circuit board processes said set of ECG data in said right-hand mode,
   the ECG lead I is taken as a negative potential difference between the second and third electrodes disposed on the back side and the front side of the case;
   the ECG lead II is taken as a potential difference between the first and third electrodes disposed on the strap and the back side of the case; and
   the ECG lead III is taken as a potential difference between the first and second electrodes disposed on the front side of the case and the strap.

18. The wristwatch of claim 1, wherein the first, second and third electrodes are used to separately contact the skin in a right upper limb, a left upper limb, and a trunk of the user to obtain said set of ECG data.

19. The wristwatch of claim 1, wherein the first, second and third electrodes are used to separately contact the skin in a right upper limb, a left upper limb, and a left lower limb of the user to obtain said set of ECG data.

* * * * *